United States Patent [19]

Armor et al.

[11] 4,046,790

[45] Sept. 6, 1977

[54] CATALYTICALLY ACTIVE COMPLEX OF TITANIUM, CYCLOPENTADIENYL LIGANDS, AND AMMONIA

[75] Inventors: John N. Armor, Morris Plains; Guido P. Pez, Boonton, both of N.J.

[73] Assignee: Allied Chemical Corporation, Morris Township, N.J.

[21] Appl. No.: 712,107

[22] Filed: Aug. 5, 1976

[51] Int. Cl.$^2$ .............................................. C07F 7/28
[52] U.S. Cl. ........................... 260/429.5; 252/431 N; 260/677 H; 260/690
[58] Field of Search ....................... 260/429.5, 429 CY

[56] References Cited

U.S. PATENT DOCUMENTS 3,776,932  12/1973  Pez .................................. 260/429.3

OTHER PUBLICATIONS

Dickens et al., Aus. J. Chem., 14, 555–561 (1961).
J.A.C.S. 94, 1219, 1226–1232, 1235, 1236 (1972).
Calderazzo, J. Organometal. Chem. 53, 179 to 182, 187 to 189, 191, 192, 195, 196 (1973).

*Primary Examiner*—Helen M. S. Sneed
*Attorney, Agent, or Firm*—Robert A. Harman

[57] ABSTRACT

A catalytically active compound or complex from the complex "bis-titanocene" (U.S. Pat. No. 3,776,932 of Dec. 4, 1973 to G. P. Pez) by reaction thereof with ammonia at low temperature and in absence of contaminants, giving a characteristic powder x-ray diffraction pattern and characteristic radiation and e.s.r. spectra.

4 Claims, No Drawings

CATALYTICALLY ACTIVE COMPLEX OF TITANIUM, CYCLOPENTADIENYL LIGANDS, AND AMMONIA

BACKGROUND OF THE INVENTION

I. Field of the Invention

This invention relates to a titanium/cyclopentadienyl ligand/ammonia complex; and to method of preparing the same from the "bis-titanocene" compound of U.S. Pat. No. 3,776,932 of Dec. 4, 1973 to G. P. Pez. Such bis-titanocene has been found to contain one of its four ligands in the form of a bridging ligand connected by a so-called pi bond to one titanium atom and by a so-called sigma bond to the other titanium atom and having the formula $C_5H_4$, as described and claimed in application Ser. No. 631,777 for reissue of said U.S. Pat. No. 3,776,932 in which all claims stand allowed. This bis-titanocene complex is referred to hereinafter as "bridged bis-titanocene".

II. Description of the Prior Art

There is considerable prior art on attempts to produce catalytically active complexes of titanium with cyclopentadienyl ligands. Such art is noted in the above cited U.S. Pat. No. 3,776,932. So far as we are aware, the art has not disclosed a complex of titanium, cyclopentadienyl ligands, and ammonia; in particular the art has not disclosed such complex which is catalytically active for reactions such as hydrogenation.

SUMMARY OF THE INVENTION

We have now discovered a catalytically active complex of titanium, cyclopentadienyl ligands and ammonia. In crystalline form, our complex has the structural formula

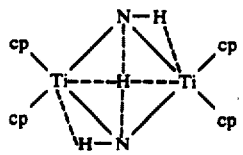

where "cp" indicates a cyclopentadienyl ligand. The positions of the cp ligands and of the Ti and N atoms have been defined by X-ray crystallography as more fully discussed below. The positions of the H atoms have been arrived at by inference from the chemical properties of the complex. The complex can be identified by its powder X-ray diffraction pattern; by its infrared spectrum; by its reflectance spectrum in the visible-near infrared region; and by its absorption spectrum in benzene solution in the visible-near infrared region.

This complex is catalytically active for hydrogenation such as hydrogenation of olefins, having the unusual characteristic of displaying activity even in the presence of amines.

The following listing shows Bragg spacings, $d$, paired with relative intensity values, $I/I_1$, for the twelve strongest lines in the Debye-Scherrer X-ray diffraction pattern of powdered crystals of the new complex, wherein Bragg spacing is in Angstrom units, and relative intensity ($I/I_1$) is that of the diffracted beam versus the major line normalized to 100:

($d$, $I/I_1$): (9.5, 45); (7.0,89); (5.74, 100); (5.50, 72); (5.20, 28); (4.79, 42); (4.27, 8); (4.02, 15); (3.91, 4); (3.71, 6); (3.38, 4); (2.69, 8).

The infrared spectrum of the subject complex shows the following absorption peaks at the indicated wave numbers (cm$^{-1}$):

| | | | |
|---|---|---|---|
| 3095 w | 1373 w | *910 M,b | 530 M |
| 2930 w, shl | 1310 w | 850 w | 488 w |
| 2895 w | *1230 w | 825 M | 458 M |
| *1585 M, b | 1135 M | 793 vst | *430 M |
| 1495 M | 1065 M | 738 st | 350 w |
| 1390 w, shl | 1020 M | | |

In the above tabulation, the letters following the wave numbers have the following meanings:

| | |
|---|---|
| w = weak | vst = very strong |
| M = medium strength | b = broad |
| st = strong | shl = shoulder |

The spectrum was recorded in mineral oil (NUJOL) and in deuterated n-hexadecane suspensions; absorption bands due to the mineral oil were thus identified and were subtracted. It shows bands characteristic of compounds containing the (cp)$_2$Ti moiety, and unique characteristic bands whereby it differs from the spectra of known compounds containing the (cp)$_2$Ti moiety, marked by an asterisk in the table, at wave numbers of 1585, 1230, 910 and 430 cm$^{-1}$.

The spectrum in the visible-near infrared region obtained by solid state reflectance shows a broad band centered at wavelength of 495 ± 10 nanometers (nm), and additional bands at 1300nm, 1540nm, 1650nm and 1860nm of intensity comparable to that at 495nm. In solution in benzene, the subject complex shows a very intense absorption band at 495nm with extinction coefficient = 3,700 per molar concentration unit-cm.; and no bands, as seen in bridged bis-titanocene, at 1130nm, 640nm and 486nm; nor any intense band between 800nm and 2,000nm.

The subject complex can be produced from bridged bis-titanocene by dissolving in toluene; freezing and degassing the solution; adding anhydrous ammonia; thawing; refreezing and removing hydrogen gas; and thawing whereby a solid settles out which solid can be purified by washing with toluene and then with n-octane.

In a preferred procedure, the subject complex is prepared by use of the starting material for bridged bis-titanocene, Ti(cp)$_2$Cl$_2$ (dicyclopentadienyl titanium dichloride). The dichloride starting material is admixed with two molecular proportions of an alkali metal such as lithium, sodium or potassium in an anhydrous, oxygen-free ethereal solvent such as diethyl ether or dimethyl ether. The operation is carried out at any convenient temperature, such as ambient or reduced temperature, in a reaction vessel from which reactive gases such as oxygen, nitrogen and carbon oxides have been removed e.g., by evacuation, or replaced with an inert atmosphere such as argon or helium gas. Naphthalene, in any quantity at least sufficient to form a catalytic quantity of the metal-naphthalene, is introduced, such quantity being for example, 5 mol percent or more based on the alkali metal. The reaction mixture is stirred to form a solution of all the ingredients.

Anhydrous ammonia is added; the solution is stirred; and the ethereal solvent is removed leaving the crude complex of titanium, cyclopentadienyl ligands and ammonia. This complex can be purified by slow crystallization from toluene.

DESCRIPTION OF THE PREFERRED EMBODIMENTS

In preferred embodiments of our process for obtaining titanium/cyclopentadienyl ligands/ammonia complex, the procedure starting from dicyclopentadienyl titanium dichloride is used. The starting material is admixed with two molecular proportions of lithium metal in diethylether solvent; a catalytic quantity such as 5—10 mol percent of naphthalene is added; and the temperature of the resulting solution is reduced until the solution is below $-100°$ C, suitably until the solution is frozen.

Ammonia is freed of water and amine impurities by thorough scrubbing by contact with sodium/potassium alloy at low temperature such as $-80°$ C. to $-50°$ C. and is passed into the cold reaction vessel where it condenses. The product, obtained upon slow warming, is purified by crystallizing at least twice from toluene solution by slow evaporation of the toluene.

The following example is illustrative of the preparation and characterization of the subject titanium/cyclopentadienyl ligands/ammonia complex and method of its preparation. Temperatures are in ° C.

EXAMPLE

Using a glove box with argon atmosphere, and glassware with valves of PTFE, 2 grams (8.1 mmoles) of Ticp$_2$Cl$_2$ was added to a two-legged reactor containing 2 equivalents (0.11 g; 16.2 mmoles) of Li powder. A catalytic amount of naphthalene (0.18 g; 1.4 mmoles) was sealed in one sidearm of the reactor, with a double vacuum tap. After evacuation of the reactor to $10^{-4}$ torr, approximately 100 ml of anhydrous diethyl ether (dried over bridged bis-titanocene) was added to the Ticp$_2$Cl$_2$ and the mixture stirred for fifteen minutes at 0°. The naphthalene was then added, and the solution was allowed to warm and was stirred overnight. The next day, the solution was frozen, ammonia (7.8 mmoles) was added; then the reaction mixture was allowed to thaw and was vigorously stirred for four days. The ether was evaporated off under vacuum, leaving a crude red residue containing impurities of lithium metal and LiCl.

Crystals of the titanium complex was grown by dissolving 1.35 grams of this crude mixture in toluene, in a 3-legged reactor. The toluene solution was filtered into the middle leg of the reactor (18° C) and about half of the toluene was slowly evaporated back into the original leg (14° C) over a period of 2 days. The toluene solution remaining in the middle leg was then filtered into the empty third leg of the reactor, and this solution was evaporated to dryness. The resulting crop of crystals in the third leg contained no Cl$^-$.

The identity of the compound was confirmed by microanalysis; and by its distinctive visible-near infrared spectrum and its powder X-ray diffraction pattern discussed above. (In the microanalysis for nitrogen, the Dumas method is modified to avoid formation of titanium nitrides, by adding Cr$_2$O$_3$.)

Preparation of crystals of titanium complex for single crystal X-ray diffraction studies To grow X-ray quality crystals, two variations of method were used.

1. Using a 2-legged reactor with a frit between the legs, 0.15 gm of the complex was dissolved in 25 ml of toluene at 23° C. The red solution was filtered into the second leg. Then the empty leg was immersed in a beaker of water through which air was bubbled. The resulting temperature differential of about 2° permitted the slow evaporation of the toluene from the filtrate. When almost all of the toluene has evaporated into the cooler leg, crystals remained in the warmer leg of the reactor. The remaining toluene layer in that leg was then filtered off, and the residue was evaporated to dryness. The resulting crystals were washed and filtered four times with about 10 ml portions of n-octane.

2. Using a 3-legged reactor fitted with two medium porosity frits, 0.2 gm of complex was dissolved in about 25 ml of toluene in the first leg. The solution was filtered into the middle leg and then slowly evaporated by immersing the middle leg in a 19° bath and the first leg, containing the residue, in a 15° bath. After 1 to 2 days, about two-thirds of the toluene in the middle leg had evaporated, with resulting formation of crystals. The toluene layer in the middle leg was poured (through the second frit) into the empty third leg and toluene was evaporated, from the crystals in the third leg, into the first leg to near dryness, using the same temperature baths as before. The crystals in each leg were washed and filtered 3 times with 10 ml portions of n-octane, which was then evaporated off under high vacuum.

The two groups of crystals obtained by the two methods were indistinguishable by microanalysis. However, the x-ray diffraction patterns indicated that the quality of the crop of crystals prepared by the second method, was much better than the crystals prepared by the first method.

The molecular structure of the complex was determined by X-Ray diffraction study of single crystals obtained as above described, based on 777 reflections with an R-factor of 8.79. It shows a framework of two titanium atoms in approximately tetrahedral environments having a separation of 3.39A and bridged by two nitrogen atoms lying symmetrically in the same plane with the titanium atoms, upon the perpendicular bisector of the line connecting the titanium atoms, as shown in the above structural formula. The unit cell is orthorhombic with parameters of $a_o=15.03$, $b_o=6.21$, $c_o=19.15$ Angstroms, and belongs to Space Group Pca2$_1$.

The above complex, having the characteristic spectra and X-ray diffraction pattern described above, can be obtained from bridged bis-titanocene in toluene solution by freezing, degasing, adding excess pure anhydrous ammonia to the cold reaction vessel, and thawing to bring about reaction with evolution of hydrogen. Such reaction has been found to fit quite closely the equation:

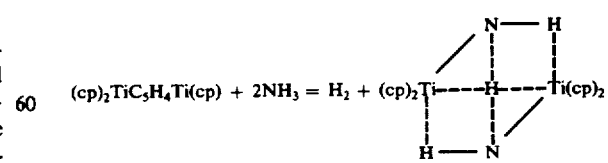

(cp)$_2$TiC$_5$H$_4$Ti(cp) + 2NH$_3$ = H$_2$ + (cp)$_2$Ti[...]Ti(cp)$_2$ where (cp) represents the cyclopentadienyl ligand.

Moreover the subject complex shows presence of at least 0.85 mole of hydride hydrogen, per mole of Ti$_2$, by conversion of excess methyl iodide, brought into reaction with the crystalline complex, to methane detected by mass spectrometry. Likewise upon addition of excess gaseous HCl, at least 0.7 mole of hydrogen is evolved per mole of $Ti_2$. Since no metal/hydride stretching frequency is observed in the spectra it is concluded that an atom of hydride hydrogen is symmetrically located between the two titanium atoms as shown in the foregoing structural formula. The two nitrogens may contribute to the bonding of such hydrogen.

When the complex is in solution, it appears it dissociates at least partially from the dimer above described to a monomer. As above noted, the bands seen by solid state reflectance at 1300 nm, 1540 nm, 1650 nm and 1860 nm are not seen in the visible-near infrared absorption spectrum of the complex when dissolved in benzene. Moreover molecular weight determination (by an isopiestic method) indicates a monomeric formula in benzene and in tetrahydrofuran. Further, the e.s.r. (electron spin resonance) derivative spectrum of the crystals, a singlet with $g$ value of 1.98 at 25° C., accords with that for known complexes of Ti(III); whereas when the complex is in solution in toluene, its e.s.r. derivative spectrum is a broadened singlet with a shoulder, and at $-100°$ C. in toluene, a new singlet appears at $g$ of about 4 and the region of $g$ about 2 splits into a quintet.

The above described complex is a highly active form of titanium. It will combine with molecular nitrogen and with carbon monoxide. If brought into contact with ethylene and hydrogen (with care not to contaminate the complex by contact with air), by condensing ethylene into a cold vessel containing a toluene solution of the complex, adding hydrogen, and warming, the complex catalyzes hydrogenation of the ethylene to ethane (detected by gas infrared spectroscopy and gas chromatography).

A similar test in which nitrogen gas was admitted into the tube containing the frozen toluene solution of the complex and ethylene, hydrogen was then added and the solution was allowed to warm, showed that nitrogen did not prevent the catalyzed hydrogenation of ethylene from occurring. Similarly, the addition of a little ethyl amine (0.5%) to the ethylene did not prevent the catalyzed hydrogenation of ethylene.

Moreover, the complex in powder form, contacted with ethylene and hydrogen, catalyzes hydrogenation of the ethylene.

A like test substituting cyclohexene for ethylene showed hydrogenation of cyclohexene is catalyzed by the subject titanium complex in toluene solution.

We claim:

1. Composition having the structural formula, when in crystalline form,

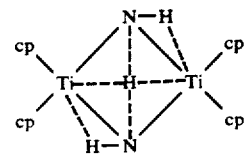

where cp indicates a cyclopentadienyl ligand; said compound, being characterized by, 1. giving a powder X-ray diffraction pattern in which the twelve strongest lines show the following Bragg spacings in Angstrom units, paired with their relative intensities ($I/I_1$):
(9.5, 45); (7.0, 89); (5.74, 100); (5.50, 72); (5.20, 28); (4.79, 42); (4.27, 8); (4.02, 15); (3.91, 4); (3.71, 6); (3.38, 4); (2.69, 8).

2. giving in suspension in mineral oil, an infrared spectrum showing bands characteristic of compounds containing the $(cp)_2Ti$ moiety and unique characteristic bands at wave numbers of 1585, 1230, 910 and 430 $cm^{-1}$; and 3. giving a solid state reflectance spectrum in the visible-near infrared region showing a broad band centered at wavelength of 495 ± 10 nm and additional bands at 1300, 1540, 1650 and 1860nm; and in benzene solution giving a visible-near infrared absorption spectrum showing a band at 495 nm and no intense bands between 800nm and 2,000nm.

2. Process of producing the composition of claim 1 which comprises admixing 2 molecular proportions of alkali metal of the group lithium, sodium and potassium with one molecular proportion of dicyclopentadienyl titanium dichloride in anhydrous, oxygen-free ethereal solvent and in an atmosphere free of reactive gases including oxygen, nitrogen, and carbon oxides; adding naphthalene in at least catalytic quantities; stirring to form a solution of all the ingredients; adding anhydrous ammonia; stirring the solution; and evaporating the ethereal solvent.

3. Process of claim 3 wherein the alkali metal is lithium; and ethereal solvent is diethyl ether; the ammonia added is free of amine impurities; and the crude product is purified and crystallized by at least twice crystallizing from toluene solution by slow evaporation of the toluene.

4. Process of producing the product of claim 1 which comprises dissolving bridged bis-titanocene in toluene; freezing and degasing the solution; adding anhydrous ammonia; thawing; refreezing and removing hydrogen gas; thawing; and recovering the solid which settles out.

* * * * *